United States Patent [19]

Wade

[11] 4,006,238
[45] Feb. 1, 1977

[54] USE OF 2-(HYDROXYALKYL)-1H-BENZ-[DE]ISOQUINOLINE-1,3(2H)-DIONES AS ANTI-ALLERGY AGENTS

[75] Inventor: Peter C. Wade, Pennington, N.J.

[73] Assignee: E. R. Squibb & Sons, Inc., Princeton, N.J.

[22] Filed: Aug. 28, 1975

[21] Appl. No.: 608,433

[52] U.S. Cl. .................................................. 424/258
[51] Int. Cl.² ....................................... A61K 31/47
[58] Field of Search ..................................... 424/258

[56] References Cited

UNITED STATES PATENTS

| 3,935,227 | 1/1976 | Wade et al. | 424/258 |
| 3,940,397 | 2/1976 | Wade et al. | 424/250 |
| 3,940,398 | 2/1976 | Wade et al. | 424/250 |
| 3,947,452 | 3/1976 | Wade et al. | 424/250 |

OTHER PUBLICATIONS

Matsuo et al., Chem. Abst., vol. 81, (1974), pp. 171,367b.

Primary Examiner—Sam Rosen
Attorney, Agent, or Firm—Lawrence S. Levinson; Merle J. Smith; Stephen B. Davis

[57] ABSTRACT

Method of treating allergies with a pharmaceutical composition containing as the active ingredient a compound or mixture of compounds of the formula

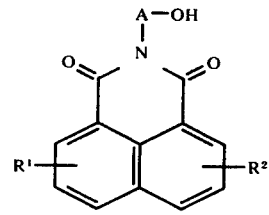

wherein $R^1$ and $R^2$ are independently selected from hydrogen, halogen, trifluoromethyl, lower alkyl, lower alkoxy, lower alkylthio, nitro, amino, or cyano; and A is a straight or branched chain alkylene of 1 to 8 carbons.

10 Claims, No Drawings

USE OF 2-(HYDROXYALKYL)-1H-BENZ[DE]ISOQUINO-LINE-1,3(2H)-DIONES AS ANTI-ALLERGY AGENTS

BACKGROUND OF THE INVENTION

Various 2-(hydroxyalkyl)-1H-benz[de]isoquinoline-1,3(2H)-diones have been prepared as chemical intermediates as note Fierz-David et al., Chem. Abst., Vol. 33, 1318[3], Nursten et al., Chem. Abst., Vol. 44, 7829b and Yanagi et al., Chem. Abst., Vol. 54, 5426h. These compounds have been of particular interest as optical brighteners and intermediates in the preparatin of optical brighteners as note Senshu et al., preparation Pat. No. 3,330,834, Schellhammer et al., U.S. Pat. No. 3,362,958 and Chiaki et al., Chem. Abst., Vol. 61, 1621a.

These compounds are also disclosed as intermediates in the preparation of pharmaceutically active compounds in U.S. Ser. Nos. 501,411 (filed Aug. 28, 1974), now U.S. Pat. No. 3,935,227; 523,293 (filed Nov. 13, 1974), now U.S. Pat. No. 3,940,397; 538,976 (filed Jan. 6, 1975), now U.S. Pat. No. 3,947,452; 538,977 (filed Jan. 6, 1975); 543,558 (filed Jan. 23, 1975), now U.S. Pat. No. 3,940,398; 581,444 (filed May 28, 1975); and 586,678 (filed June 13, 1975).

SUMMARY OF THE INVENTION

This invention relates to the use of certain 2-(hydroxyalkyl)-1H-benz[de]isoquinoline-1,3(2H)-diones as anti-allergy agents. These compounds are of the formula

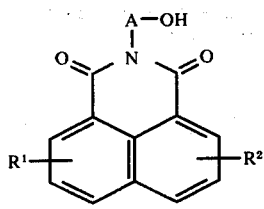
(I)

The symbols have the following meaning in formula I and throughout this specification.

$R^1$ and $R^2$ are each independently selected from hydrogen, halogen, trifluoromethyl, lower alkyl, lower alkoxy, lower alkylthio, nitro, amino, and cyano.

A is straight or branched chain alkylene of 1 to 8 carbons.

DETAILED DESCRIPTION OF THE INVENTION

The various groups represented by the symbols have the meanings defined below and these definitions are retained throughout this specification.

The lower alkyl groups referred to throughout this specification include straight or branched chain hydrocarbon groups containing 1 to 4 carbons. Examples of the type of groups contemplated are methyl, ethyl, propyl, isopropyl, butyl, etc. The lower alkoxy groups include such lower alkyl groups attached to an oxygen, e.g., methoxy, ethoxy, propoxy, etc. The lower alkylthio group include such lower alkyl groups attached to a sulfur, e.g., methylthio, ethylthio, etc.

Straight or branched chain alkylene of 1 to 8 carbons is intended to include group such as —(CH$_2$)$_n$— wherein n is 1 to 8,

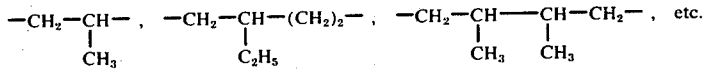

The term "halogen" as used throughout this specification refers to fluorine, chlorine, bromine and iodine, with fluorine, chlorine and bromine being preferred and chlorine being most preferred.

Preferred compounds of this invention are those having the formula

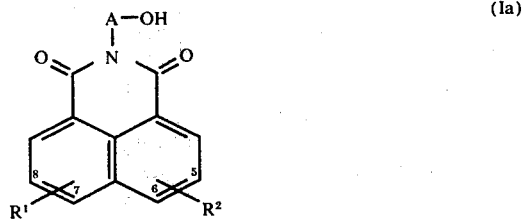
(Ia)

wherein $R^1$ and $R^2$ are independently selected from hydrogen, Cl, Br, F, methyl and methoxy and are located at the 7- or 8-position or the 5- or 6-position respectively; and A is straight or branched chain alkylene of 1 to 6 carbons.

Most preferred are the compounds of formula Ia wherein $R^1$ and $R^2$ are both hydrogen and A is straight chain alkylene of 1 to 5 carbons.

The compounds of formula I can be prepared by any of the various methods taught in the literature.

The preferred method of preparation where A is straight or branched chain alkylene of 2 to 8 carbons is to react at the reflux temperature of the solvent for several hours a substituted naphthalic anhydride of the formula

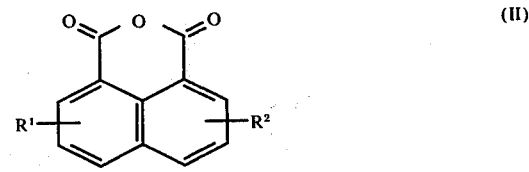
(II)

with an alkanolamine of the formula $$H_2N—A—OH \qquad (III)$$

in a solvent such as water, butanol, dioxane, dimethylformamide, etc.

The preferred method of preparation wherein A is —CH$_2$— is to react at elevated temperature a naphthalimide of the formula

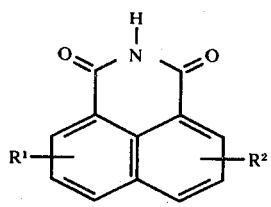
(IV)

suspended in a polar organic solvent such as dimethylformamide (DMF) and a source of formaldehyde such as aqueous formaldehyde or paraformaldehyde.

The various starting materials such as the substituted anhydrides of formula II or substituted naphthalimides of formula IV are known in the art or are readily obtainable by known procedures.

The compounds of formula I wherein either or both $R^1$ and $R^2$ are amine are prepared by reducing the corresponding nitro substituted compound with a reducing agent such as hydrogen over a palladium catalyst or a suitable chemical reducing agent. This is preferably done as the last stage in the reaction procedures described above.

The compounds of formula I are useful in treating various allergic conditions in mammalian species such as mice, cats, rats, dogs, etc. when administered in amounts ranging from about 1 mg. to bout 500 mg. per kg. of body weight per day. The compounds can be used prophylactically or therapeutically to treat various allergic and immunological disorders and in particular to treat certain types of asthma, hay-fever, and rhinitis. A preferred dosage regimen would be from about 3 mg. to about 200 mg. per kg. of body weight per day administered in a single or plurality of divided doses.

The compounds of formula I are anti-allergics which inhibit the effects of certain antigen-antibody reactions and in particular inhibit the release of mediators such as histamine. The anti-allergy activity of these compounds is determined by the reaginic antibody induced passive cutaneous anaphylaxis (PCA) reaction in rats. (See Bach, Immediate Hypersensitivity: Laboratory Models and Experimental Findings, Ann. Rep. Med. Chem., 7: 238–248 (1972), for a discussion of the predictability of clinical efficacy of compounds active in the PCA).

A compound or mixture of compounds of formula I may be administered by the inhalation of an aerosol or powder as note U.S. Pat. No. 3,772,336 (i.e., breathing finely divided particles of the active ingredient into the lungs), orally, or parenterally. Powders can be prepared by comminuting the active ingredient with a similarly comminuted diluent such as starch or lactose. Suitable oral forms include capsules, tablets, and syrups and suitable parenteral form includes a sterile injectable. Such unit dosage forms are prepared by compounding with a conventional vehicle, excipient, binder, preservative, stabilizer, flavoring agent or the like as called for by acceptable pharmaceutical practice. Also, the compounds of formula I may be formulated with other pharmaceutically active compounds such as bronchodilators, steroids, antihistamines, etc.

The following examples are illustrative of the invention and represent preferred embodiments. All temperatures are on the centigrade scale.

EXAMPLE 1

2-(Hydroxymethyl)-1H-benz[de]isoquinoline-1,3(2H)-dione 30 g. (0.15 mole) of 1,8-naphthalimide and 12.5 ml. of 37% aqueous formaldehyde (0.17 mole) are combined in 100 ml. of dimethylformamide and heated on a hot plate (90°–110°) until all the materials dissolve. The solution is then allowed to stand overnight at 25°. The resulting precipitate is filtered off, washed with water and recrystallized from dioxane. This material is dried overnight at 25° (0.1 mm.) to yield 26.4 g. of the titled compound which has an indistinct melting point.

EXAMPLE 2

2-(2-Hydroxyethyl)-1H-benz[de]isoquinoline-1,3(2H)-dione 50 g. (0.252 mole) of naphthalic anhydride and 16 g. (0.262 mole) of ethanolamine are refluxed for three hours in 200 ml. of water (the solution is never complete). After cooling to 25° the water is decanted off and the residue recrystallized from 95% ethanol to yield 47.8 g. of 2-(2-hydroxyethyl)-1H-benz[de]isoquinoline-1,3(2H)-dione; m.p. 172°–173°.

EXAMPLE 3

2-(3-Hydroxypropyl)-1H-benz[de]iosquinoline-1,3(2H)-dione

Following the procedure of example 2 but substituting propanolamine for the ethanolamine one obtains the titled compound; m.p. 115°–118°.

EXAMPLE 4

2-(4-Hydroxybutyl)-1H-benz[de]isoquinoline-1,3(2H)-dione

Following the procedure of example 2 but substituting butanolamine for the ethanolamine one obtains the titled compound; m.p. 105°–108.5°.

EXAMPLE 5

2-(5-Hydroxypentyl)-1H-benz[de]isoquinoline-1,3(2H)-dione 19 g. (0.96 mole) of naphthalic anhydride and 10 g. (0.097 mole) of pentanolamine are refluxed for 2 hours in 200 ml. of water (the solution is never complete). After cooling to 25° the water is decanted off and the residue is taken up in CHCl₃ and washed with 10% NaOH. The solvent is removed under vacuum and the residue is taken up in a hot mixture of ethanol:hexane (1:2). The mixture is cooled slowly with seed crystals being added frequently during the cooling. Once crystallization has been initiated the mixture is cooled to 0° for several hours. The crystals are filtered off and dried at 25° (0.1 mm.) for 12 hours to yield 11.5 g. of the titled compound; m.p. 96.5°–97.5°.

EXAMPLES 6–13

Following the procedure of example 2 but substituting the alkanolamine shown in Col. I for the ethanolamine the following products are obtained wherein A is the radical shown in Col. II.

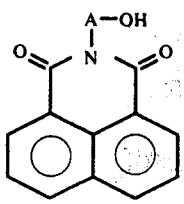

| Ex. | Col. I | Col. II |
|---|---|---|
| 6 | $H_2N-(CH_2)_6-OH$ | $-(CH_2)_6-$ |
| 7 | $H_2N-(CH_2)_7-OH$ | $-(CH_2)_7-$ |
| 8 | $H_2N-(CH_2)_8-OH$ | $-(CH_2)_8-$ |
| 9 | $H_2N-CH_2-\underset{CH_3}{CH}-CH_2-OH$ | $-CH_2-\underset{CH_3}{CH}-CH_2-$ |
| 10 | $H_2N-\underset{CH_3}{CH}-(CH_2)_3-OH$ | $-\underset{CH_3}{CH}-(CH_2)_3-$ |
| 11 | $H_2N-(CH_2)_3-\underset{CH_3}{CH}-OH$ | $-(CH_2)_3-\underset{CH_3}{CH}-$ |
| 12 | $H_2N-CH_2-\underset{C_3H_7}{CH}-(CH_2)_2-OH$ | $-CH_2-\underset{C_3H_7}{CH}-(CH_2)_2-$ |
| 13 | $H_2N-\underset{CH_3}{CH}-CH_2-\underset{CH_3}{CH}-OH$ | $-\underset{CH_3}{CH}-CH_2-\underset{CH_3}{CH}-$ |

EXAMPLES 14–39

Following the procedure of example 2 but employing the substituted naphthalic anhydride shown below in Col. I one obtains the product shown in Col. II.

| Ex. | $X^1$ | $X^2$ | $X^3$ | $X^4$ | $X^5$ | $X^6$ |
|---|---|---|---|---|---|---|
| 14 | H | H | Cl | H | H | H |
| 15 | H | Cl | H | H | H | H |
| 16 | H | Br | H | H | H | H |
| 17 | H | F | H | H | H | H |
| 18 | H | I | H | H | H | H |
| 19 | H | Cl | H | H | Cl | H |
| 20 | Br | H | H | H | H | H |
| 21 | H | H | Cl | Cl | H | H |
| 22 | H | H | $CH_3$ | H | H | H |
| 23 | H | H | $C_2H_5$ | H | H | H |
| 24 | H | H | $i-C_3H_7$ | H | H | H |
| 25 | H | H | $CH_3$ | $CH_3$ | H | H |
| 26 | H | H | $OCH_3$ | H | H | H |
| 27 | H | H | $OC_2H_5$ | H | H | H |
| 28 | H | H | $OC_3H_7$ | H | H | H |
| 29 | H | H | $OCH_3$ | $OCH_3$ | H | H |
| 30 | H | $NO_2$ | H | H | H | H |
| 31 | H | H | $NO_2$ | H | H | H |
| 32 | H | $CF_3$ | H | H | H | H |
| 33 | H | H | $CF_3$ | H | H | H |
| 34 | H | CN | H | H | H | H |
| 35 | H | H | CN | H | H | H |
| 36 | H | H | $NH_2$ | H | H | H |
| 37 | H | $NH_2$ | H | H | H | H |
| 38 | H | $SC_2H_5$ | H | H | H | H |
| 39 | H | H | $SCH_3$ | H | H | H |

Similarly, by employing the substituted anhydrides of examples 14–39 within the procedure of examples 3–13, other compounds within the scope of the invention are obtained.

Also, by following the procedure of example 1 but employing a substituted naphthalimide of formula IV wherein the substituents are those listed under the headings $X^1, X^2, X^3, X^4, X^5$ and $X^6$ in examples 14–39, other compounds within the scope of the invention are obtained.

EXAMPLES 40–44

The following table shows the activity of certain compounds from previous examples on the reaginic antibody induced passive cutaneous anaphylaxis (PCA) reaction in rats.

| Compound | Percent Inhibition |
|---|---|
| 2-(Hydroxymethyl)-1H-benz[de]isoquinoline-1,3(2H)-dione | 50 (average of two experiments) |
| 2-(2-Hydroxyethyl)-1H-benz[de]isoquinoline-1,3(2H)-dione | 36 |
| 2-(3-Hydroxypropyl)-1H-benz[de]isoquinoline-1,3(2H)-dione | 52 (average of four experiments) |
| 2-(4-Hydroxybutyl)-1H-benz[de]isoquinoline-1,3(2H)-dione | 53 (average of two experiments |
| 2-(5-Hydroxypentyl)-1H-benz[de]isoquinoline-1,3(2H)-dione | 8 |

The experimental procedure employed is as follows. A male rat is given an intradermal injection on one flank of 0.05 ml. of antibody (reaginic) (anti-Egg Albumin). 24 hours later two doses of test compound (75 mg./kg.) are administered intraperitoneally, one dose ninety minutes and the other ten minutes prior to a 0.5 ml. intravenous injection of an antigen challenge (equal portions of Egg Albumin 4 mg./ml. and 1% Evans Blue Dye). Thirty minutes after the challenge intravenous injection, the rat is sacrificed and the skin on the back of the animal is reflected revealing blue-dye marked edema spots. A score is obtained according to the formula Total score = (diameter) × (intensity)

wherein the intensity of the spot is rated on a scale of 1 to 3 as follows

1+ = light intensity
2+ = moderate intensity
3+ = strong intensity and the diameter is determined by averaging in millimeters two measured diameters of the reaction.

The percent inhibition is calculated by comparing the scores obtained in both compound and non-compound treated animals according to a pre-determined standard curve relationship between score and the quantity of antibody used to elicit the reaction.

What is claimed is:

1. The method of treating an allergic mammalian host which comprises administering an effective amount of an antiallergy pharmaceutical composition comprising a pharmaceutically acceptable carrier and an anti-allergy compound or a mixture of compounds having the formula

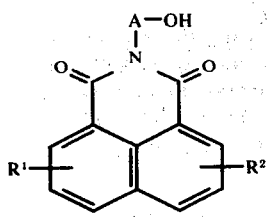

wherein $R^1$ and $R^2$ are independently selected from the group consisting of hydrogen, halogen, trifluoromethyl, lower alkyl of 1 to 4 carbons, lower alkoxy of 1 to 4 carbons, lower alkylthio of 1 to 4 carbons, nitro, amino, and cyano; and A is a straight or branched chain alkylene of 1 to 8 carbons.

2. The method of claim 1 wherein said anti-allergy compound is present in an amount ranging from about 1 mg. to about 500 mg. per kg. of body weight of the mammal.

3. The method of claim 2 wherein said composition is administered orally, injectably or by inhalation.

4. The method of claim 2 wherein said anti-allergy compound is of the formula

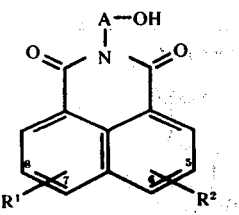

wherein $R^1$ and $R^2$ are independently selected from the group consisting of hydrogen, Cl, Br, F, $CH_3$, and $OCH_3$ and are located at the 7- or 8-position and the 5- or 6-position respectively; and A is a straight or branched chain alkylene of 1 to 6 carbons.

5. The method of claim 2 wherein said anti-allergy compound is of the formula

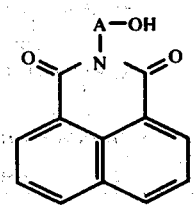

wherein A is straight chain alkylene of 1 to 5 carbons.

6. The method of claim 5 wherein said anti-allergy compound is 2-(hydroxymethyl)-1H-benz-[de]isoquinoline-1,3(2H)-dione.

7. The method of claim 5 wherein said anti-allergy compound is 2-(2-hydroxyethyl)-1H-benz-[de]isoquinoline-1,3(2H)-dione.

8. The method of claim 5 wherein said anti-allergy compound is 2-(3-hydroxypropyl)-1H-benz-[de]isoquinoline-1,3(2H)-dione.

9. The method of claim 5 wherein said anti-allergy compound is 2-(4-hydroxybutyl)-1H-benz-[de]isoquinoline-1,3(2H)-dione.

10. The method of claim 5 wherein said anti-allergy compound is 2-(5-hydroxypentyl)-1H-benz-[de]isoquinoline-1,3(2H)-dione.

* * * * *